Nov. 23, 1937. J. H. NICOLAS Plant Pat. 264
ROSE
Filed March 24, 1937
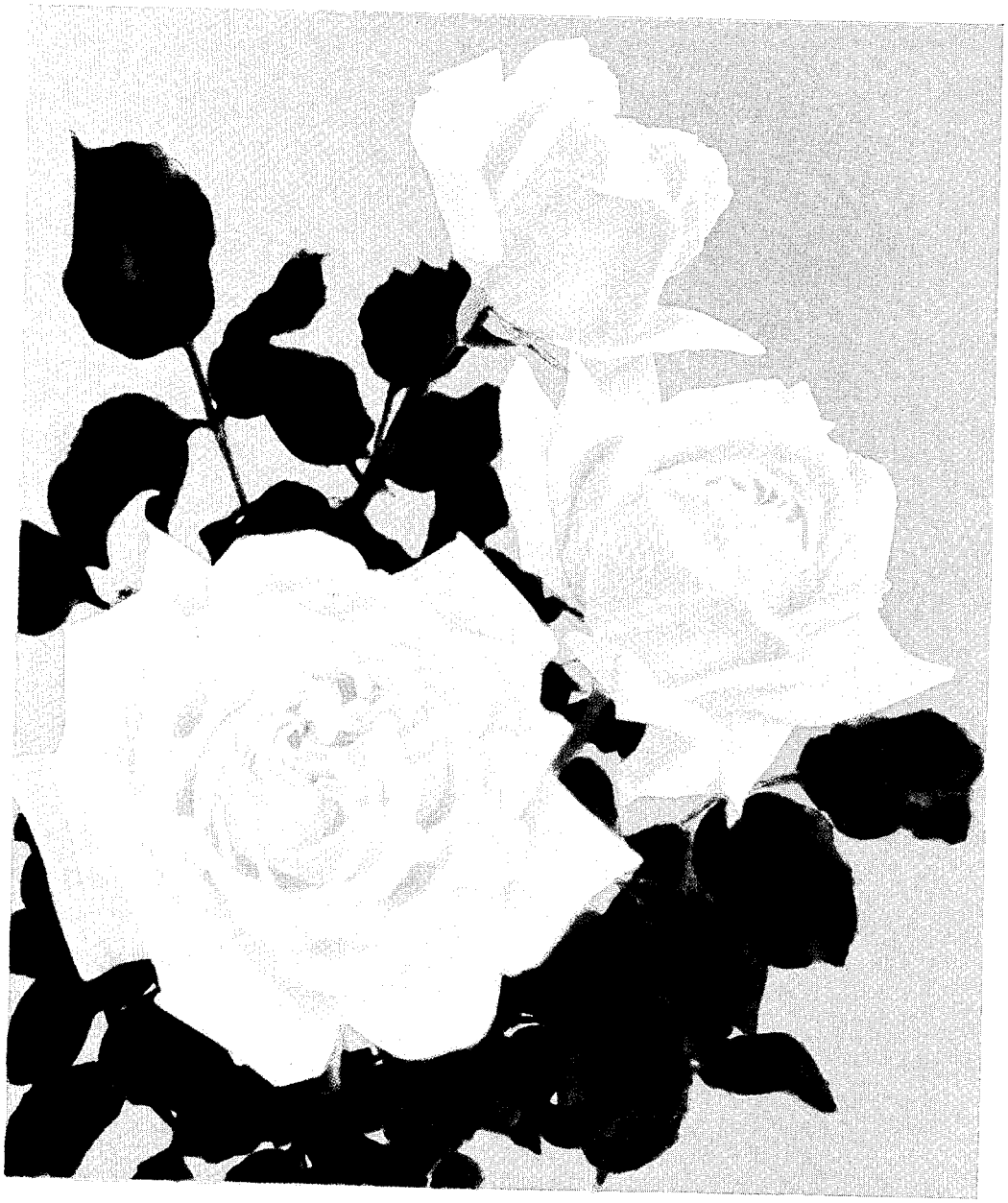
Inventor
J. H. Nicolas
By Robb & Robb
Attorneys Patented Nov. 23, 1937

UNITED STATES PATENT OFFICE

264

ROSE

Jean H. Nicolas, Newark, N. Y., assignor to Jackson & Perkins Company, Newark, N. Y.

Application March 24, 1937, Serial No. 132,865

1 Claim. (Cl. 47—61)

The present invention relates to a new and distinct variety of rose plant having as its primary objective the origination of a continuous blooming rose of strong constitution and hardiness throughout a larger territory than the normal Hybrid Tea.

To obtain these dominating characters, I selected as the seed bearer the well known variety "Joanna Hill", a Hybrid Tea noted for its profuseness of blooming indoors and outdoors and great range of colors which may be anticipated of its progeny, and for the pollen parent "S. M. Gustave V", known as an everblooming Hybrid Perpetual of great vigor best adapted for use as a pillar. In the selection of the latter parent, I had in mind the characteristics of its immediate parentage "Frau Karl Druschki", a vigorous Hybrid Perpetual of great hardiness, and "Avoca", a large flowering climber, notably one of the hardiest modern Hybrid Perpetuals.

From this cross, first mentioned, I raised five seedlings, four of which are vigorous climbers, showing the dominant influence of the pollen parent, and the fifth is the present new variety herein disclosed. This fifth seedling remains a bush plant, but again shows the dominant influence of the pollen parent in its hardwood, robustness and winter hardiness.

In this cross of known varieties, I have produced an everblooming rose of an entirely new type of plant and color, particularly useful for planting in sections where the normal Hybrid Tea usually suffers winter injury.

The bloom is large and full to the center, borne by long stems well clothed with a dark holly foliage by which I mean that the foliage has the color and undulating appearance of holly leaves. Its general tonality is buff with opalescent variations of which there is no true representation in any standard color chart. As nearly as can be found, it approaches "Chamois", Gravereaux chart No. 2, first column, Plate II, which color system is referred to in color designations herein, except where obviously the ordinary dictionary definition is meant.

Over a period of time, this new variety has been budded and rebudded and always the reproductions come true to form. Thorough tests have been made in various sections of the United States and Canada and from these the dominating characteristics herein referred to have been noted.

The following is a detailed description of my new variety:—

Parentage:

*Seedling.*—Seed parent—Joanna Hill. Pollen parent—S. M. Gustave V.

Classification:

*Botanic and commercial.*—Hybrid Tea.

*Flower*

Blooming habit:

*Location where observations were made.*—Various fields of Jackson and Perkins Company and test gardens throughout the United States.

*Recurrent.*—Continuous.

Bud:

*Size.*—Very large.

*Form.*—Ovoid.

Unaffected by wet or hot weather.

*Color.*—When sepals first divide—nasturtium orange. When petals begin to unfurl—nasturtium. When half blown—nasturtium with opalescent reflexes.

*Sepals.*—Smooth edge, curl back when half open.

*Calyx.* — Shape — funnel. Size — broad, long. Aspect—smooth. Odor when rubbed—none.

*Peduncle.* — Length — medium. Aspect — smooth. Color — medium green. Strength — erect, heavy.

*Opening.*—Bud opens well. Is not affected by adverse conditions.

Bloom:

*Size.*—Very large. Average size when fully expanded 4 inches.

*Borne.*—Singly.

*Stems.*—Long, strong.

*Form.*—When first open—globular. Permanence—retains its form to the end.

*Petalage.*—Very double (many petals and stamens hidden). Number of petals under normal conditions—75 to 100.

*Color.*—Center of flower—opalescent nasturtium. Outer petals—opalescent nasturtium. Base of petals (aiglet)—lemon. Inside of petals — opalescent nasturtium. Reverse of petals—chamois. General tonality from a distance—chamois nasturtium.

*Variegations.*—None.

*Discoloration.*—General tonality at end of first and second days—no discoloration. Third day—generally lighter.

Petals:

*Texture.*—Thick, unaffected by wet or hot weather.

*Appearance.* — Inside — satiny. Outside—shiny.

*Form.*—Round, some notched.

*Arrangement.* — Imbricated (regularly arranged shinglelike). Petaloids in center—few, large.

*Persistence.*—Drop of cleanly.

*Fragrance.*—Moderate.

*Nature.*—Tea (Average Hybrid Tea Scent).

*Lasting quality.*—On the plant and as cut flower—very long.

Genital organs:

*Stamens, Anthers.*—Large. Color—yellow. Arrangement—Mixed with petaloids.

*Stamens, filaments (threads).*—Short. Color—white.

*Pollen.*—Lemon.

*Styles.*—Loosely separated, uneven length. Medium length, heavy.

*Stigmas.*—White.

*Ovaries.*—Some protruding from calyx.

Fruit:

Variety is generally sterile with its own pollen.

*Form.*—Seeds protruding.

*Aspect.*—Smooth.

*Color at maturity.*—Orange.

*Sepals.*—Caducous (soon falling).

*Plant*

Form:

Bush.

Growth:

Very vigorous.

Foliage:

Generally five leaflets, sometimes 7.

*Size.*—Large.

*Quantity.*—Abundant.

*Color.*—New foliage—upper side—dark green; under side—lighter green. Old foliage—dark green.

*Shape.*—Oval pointed.

*Texture.*—Upper side—glossy. Under side—Smooth. Ribs and veins—prominent.

*Edge.*—Serrated (saw toothed).

*Serration.*—Single, small.

*Rachis.* — Color — reddish. Under side—prickles.

*Stipules.*—Medium, smooth.

*Disease resistance.*—Resistant.

Wood:

*New wood.*—Color — light green. Bark—smooth.

*Old wood.*—Color—green. Bark—smooth.

Thorns: (Thorns are divided into thorns, prickles and short needles).

*Thorns.*—Quantity—On main stalks from base, ordinary; on laterals from stalk, few. Form—narrow base, medium length hooked downward. Color when young — red. Position—irregular.

*Prickles.*—None.

*Short needles.*—None.

I claim:

A new and distinct variety of rose plant characterized as to novelty by its strong constitution, hardiness in a larger territory than the normal Hybrid Tea, dark holly foliage on long stems, continuity and profuseness of bloom, and the nasturtium color of the blooms with opalescent variations, substantially as shown and described.

JEAN H. NICOLAS.